United States Patent
Rohr et al.

[11] Patent Number: 4,629,498
[45] Date of Patent: Dec. 16, 1986

[54] NOVEL PHENOXYPHENOXYALKANOYLTHIOAMIDES AS HERBICIDES

[75] Inventors: Otto Rohr, Therwil, Switzerland; Georg Pissiotas, Lörrach, Fed. Rep. of Germany

[73] Assignee: Ciba-Geigy Corporation, Ardsley, N.Y.

[21] Appl. No.: 729,891

[22] Filed: May 2, 1985

Related U.S. Application Data

[63] Continuation of Ser. No. 462,259, Jan. 31, 1983.

[30] Foreign Application Priority Data

Feb. 12, 1982 [CH] Switzerland .................. 886/82

[51] Int. Cl.$^4$ .................. C07C 153/05; A01N 31/00
[52] U.S. Cl. .................................. 71/98; 564/74
[58] Field of Search ........................ 71/98; 564/74

[56] References Cited

U.S. PATENT DOCUMENTS

| | | | |
|---|---|---|---|
| 3,080,225 | 3/1963 | Wilson | 71/124 |
| 3,442,945 | 5/1969 | Olin | 564/214 |
| 3,954,442 | 5/1976 | Becker | 71/108 |

FOREIGN PATENT DOCUMENTS

| | | | |
|---|---|---|---|
| 1092240 | 6/1980 | Canada | 71/98 |
| 0003295 | 8/1979 | European Pat. Off. | 71/98 |
| 0014880 | 9/1980 | European Pat. Off. | 71/98 |
| 34120 | 8/1981 | European Pat. Off. | 180/21 |
| 2613697 | 10/1977 | Fed. Rep. of Germany | 71/98 |
| 1572125 | 7/1980 | United Kingdom | 71/98 |

Primary Examiner—Paul J. Killos
Attorney, Agent, or Firm—Edward McC. Roberts; Kevin T. Mansfield

[57] ABSTRACT

Phenoxyphenoxyalkanoylthioamides of the formula I

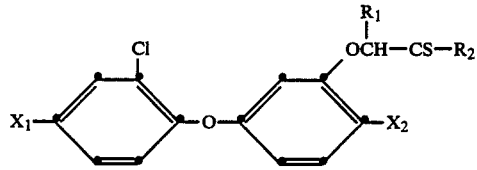

wherein $X_1$ is chlorine or trifluoromethyl, $X_2$ is chlorine or nitro, $R_1$ is $C_1$–$C_4$ alkyl, and $R_2$ is the amino group or an amidino group

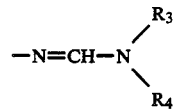

wherein each of $R_3$ and $R_4$ independently is hydrogen or $C_1$–$C_4$ alkyl or taken together they form a $C_4$–$C_5$ alkylene chain, have herbicidal and growth regulating properties. They are suitable for selectively controlling weeds in crops of useful plants, especially in cereals and rice.

12 Claims, No Drawings

NOVEL PHENOXYPHENOXYALKANOYLTHIOAMIDES AS HERBICIDES

This application is a continuation of application Ser. No. 462,259, filed Jan. 31, 1983.

The present invention relates to novel phenoxyphenoxyalkanoylthioamides, to the preparation thereof, to herbicidal compositions which contain them, to the use of these novel compounds as herbicides, and to a method of controlling weeds selectively in crops of useful plants, especially in cereals and rice.

The phenoxyphenoxyalkanoylthioamides have the formula I

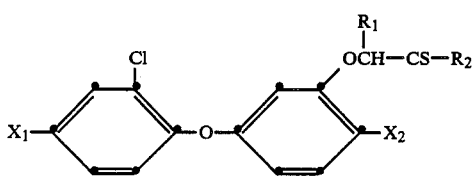
(I)

wherein
$X_1$ is chlorine or trifluoromethyl,
$X_2$ is chlorine or nitro,
$R_1$ is $C_1$–$C_4$alkyl, and
$R_2$ is the amino group or an amidino group

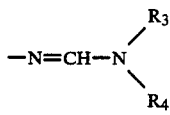

wherein each of $R_3$ and $R_4$ independently is hydrogen or $C_1$–$C_4$alkyl or taken together they form a $C_4$–$C_5$alkylene chain.

Preferred alkyl groups $R_1$, $R_3$ and $R_4$ are methyl and ethyl.

Phenoxyphenoxyalkanocarboxylic acid derivatives with herbicidal properties are known, e.g. from German Offenlegungsschrift specification Nos. 2 223 894, 2 433 004, 2 531 643, 2 639 796 and 2 732 442. Some are used as selective herbicides in crops of cereals, but their action is not always satisfactory because assured weed control requires concentrations which are toxic to sensitive plants such as sorghum and rice.

The phenoxyphenoxyalkanoylthioamides of the formula I, when used at low rates of application, destroy weeds in cereals and rice or damage them so that their growth is stunted and they are no longer able to compete with the cultivated plants.

In addition, the compounds of formula I have pronounced growth regulating, in particular growth inhibiting, properties. They inhibit the growth of both monocots and dicots.

Particularly active compounds are the amides of the formula Ia

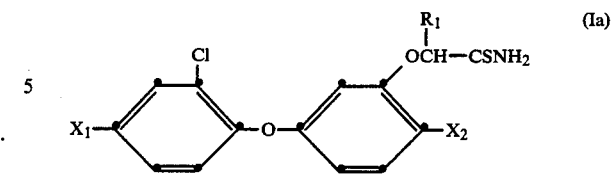
(Ia)

wherein $R_1$ is methyl or ethyl and $X_1$ and $X_2$ are as defined above, and the amidines of the formula Ib

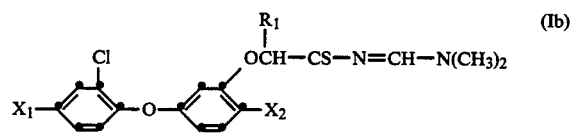
(Ib)

wherein $R_1$ is methyl or ethyl and $X_1$ and $X_2$ are as defined above.

Individual compounds meriting particular interest are:
α-[-3-(2-chloro-4-trifluoromethylphenoxy)-6-chlorophenoxy]thiopropionylamide,
α-[3-(2-chloro-4-trifluoromethylphenoxy)-6-chlorophenoxy]thiopropionyldimethylamidine,
α-[3-(2,4-dichlorophenoxy)-6-chlorophenoxy]-thiopropionyl]amide,
α-[3-(2,4-dichlorophenoxy)-6-chlorophenoxy]thiopropionyldimethylamidine,
α-[3-(2,4-dichlorophenoxy)-6-chlorophenoxy]thiobutyrylamide,
α-[3-(2,4-dichlorophenoxy)-6-chlorophenoxy]thiobutyryldimethylamidine,
α-3-(2,4-dichlorophenoxy)-6-nitrophenoxy]thiopropionylamide,
α-[3-(2,4-dichlorophenoxy)-6-nitrophenoxy]thiopropionyldimethylamidine.

The phenoxyphenoxyalkanoylthioamides of the formula I are stable compounds whose handling and application cause no problems. Proposed rates of application are in the range from 0.05 to 5 kg per hectare, with the preferred range being from 0.1 to 1.5 kg/ha.

The phenoxyphenoxyalkanoylthioamides of the formula I are prepared in a manner known per se by condensing a 3-(2-chlorophenoxy)phenol of the formula II

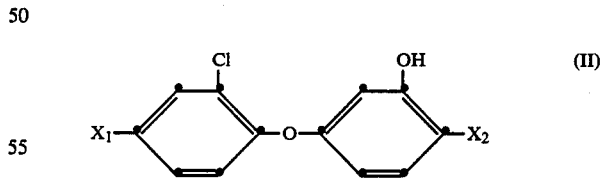
(II)

wherein $X_1$ and $X_2$ have the given meanings, with an α-halo($C_1$–$C_4$)alkanoylnitrile of the formula III

(III)

wherein Hal is a halogen atom, preferably a chlorine or bromine atom, and $R_1$ has the given meaning, and treating the resultant α-[3-(2-chlorophenoxy)phenoxy]alkanoylnitrile of the formula IV

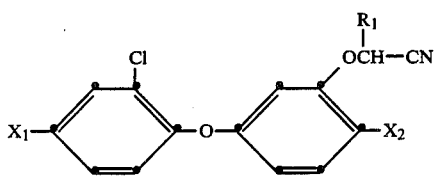

wherein $X_1$, $X_2$ and $R_1$ have the given meanings, in an inert basic solvent, with hydrogen sulfide until the nitrile is converted to the thioamide and, if desired, reacting the amide of the formula Ia

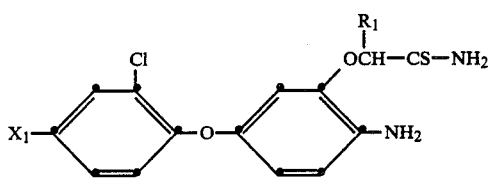

wherein $X_1$, $X_2$ and $R_1$ have the given meanings, with a formamide of the formula V

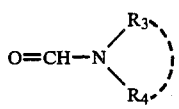

wherein $R_3$ and $R_4$ have the given meanings, or with a reactive derivative thereof, in the presence of an inert organic solvent and of a basic condensing agent.

Examples of suitable derivatives of the formamidine of the formula V are: dimethylformamide dimethylacetal, dimethylformamide diethylacetal, pyrrolidinoformamide dimethylacetal, piperidinoformamide diethylacetal.

The reaction is carried out in an inert organic solvent in a temperature range from room temperature to 200° C., under normal pressure or in an autoclave under excess pressure.

Examples of suitable basic solvents are pyridine, collidine, dimethylformamide.

Examples of suitable basic condensing agents are organic tertiary amines such as triethylamine, or organic bases such as sodium carbonate or bicarbonate or potassium carbonate.

Most of the starting phenoxyphenols are known and the preparation thereof has been described in recent patent literature. Reference is made in this connection to German Offenlegungsschrift specification Nos. 2 223 894, 2 433 066, 2 433 067, 2 531 643 and 2 639 796.

The invention also relates to herbicidal and growth regulating compositions which contain a novel compound of the formula I, as well as to methods of controlling weeds pre- and postemergence and of controlling the growth of monocot and dicot plants, in particular grasses.

The compounds of the formula I are used in unmodified form or, preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering or pouring, are chosen in accordance with the intended objectives and the prevailing circumstances.

The formulations, i.e. the compositions containing the compound (active ingredient) of the formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalates or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethyl sulfoxide or dimethyl formamide, as well as epoxidised vegetable oils such as epoxidised coconut oil or soybean oil; or water.

The solid carriers used e.g. for dusts and dispersible powders, are normally natural mineral fillers such as calcite, talcum kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepolite or bentonite; and suitable norsorbent carriers are materials such as calcite or sand. In addition, a great number of preganulated materials of inorganic or organic nature can be used, e.g. especially dolomite or pulverised plant residues.

Depending on the nature of the compound of the formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyl laurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

. Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one $C_8$-$C_{22}$alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in the following publications: "McCutcheon's Detergents and Emulsifiers Annual", MC Publishing Corp., Ringwodd, N.J., 1979; Sisely and Wood, "Encyclopedia of Surface Active Agents", Chemical Publishing Co. Inc., New York, 1964.

The pesticidal formulations usually contain 0.1 to 95%, preferably 0.1 to 80%, of a compound of the formula I, 1 to 99.9% of a solid or liquid adjuvant, and 0 to 25%, preferably 0.1 to 25%, of a surfactant.

Preferred formulations are composed in particular of the following constituents (%=percentage by weight):

Emulsifiable concentrates active ingredient: 1% to 20%, preferably 5 to 10%
surfactant: 5% to 30%, preferably 10 to 20%
liquid carrier: 50% to 94%, preferably 70 to 85%

Dusts active ingredient: 0.1 to 10%, preferably 0.1 to 1%
solid carrier: 99.9 to 90%, preferably 99.9 to 99%

Suspension concentrates active ingredient: 5 to 75%, preferably 10 to 50%
water: 94 to 25%, preferably 90 to 30%
surfactant: 1 to 40%, preferably 2 to 30%

Wettable powders active ingredient: 0.5 to 90%, preferably 1 to 80%
surfactant: 0.5 to 20%, preferably 1 to 15% solid carrier: 5 to 95%, preferably 15 to 90%

Granulates active ingredient: 0.5 to 30%, preferably 3 to 15%
solid carrier: 99.5 to 70%, preferably 97 to 85%.

Whereas commercial products will be preferably formulated as concentrates, the end user will normally employ dilute formulations. The formulations can be diluted to a concentration as low as 0.001%. The rates of application are normally 0.01 to 10 kg a.i./ha, preferably 0.025 to 5 kg a.i./ha.

The compositions may also contain further ingredients such as stabilisers, antifoams, viscosity regulators, binders, adhesives, as well as fertilisers or other active compounds, in order to attain special effects.

EXAMPLE 1

Preparation of α-[3-(2'-chloro-4'-trifluoromethylphenoxy)-6-chlorophenoxy]thiopropionylamide

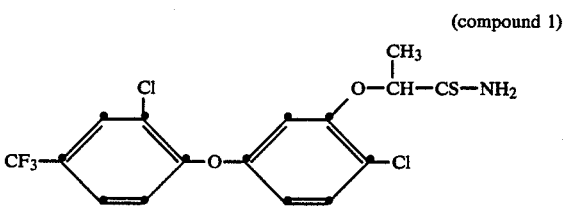

(compound 1)

(a) A mixture of 60 g of 3-hydroxy-2',4-dichloro-4'-trifluoromethyldiphenyl ether, 42.9 g of bromopropionitrile, 51.5 g of potassium carbonate and a trace of potassium iodide is stirred overnight at a bath temperature of 100° C. After it has cooled, the reaction mixture is filtered and the filtrate is concentrated, affording 55 g of α-[3-(2'-chloro-4'-trifluoromethylphenoxy)-6-chlorophenoxy]propionitrile in the form of a reddish brown oil with a refractive index of $n_D^{24}$=1.5291.

(b) 37.6 of the propionitrile obtained in (a) are dissolved in 35 ml of pyridine. To this solution are added 14 ml of triethylamine and then hydrogen sulfide is passed into the solution over 2 hours. When the reaction is complete, the solution is poured into water and the organic phase is extracted with ethyl acetate. The extract is dried over sodium sulfate, the solvent is removed by evaporation, and the residue is chromatographed over a column of silica gel to give the title compound in the form of a red oil which crystallises on standing. Yield: 37 g of crystalline product with a melting point of 83°–89° C.

EXAMPLE 2

Preparation of α-[3-(2'-chloro-4'-trifluoromethylphenoxy)-6-chlorophenoxy]thiopropionyl-dimethylamidine

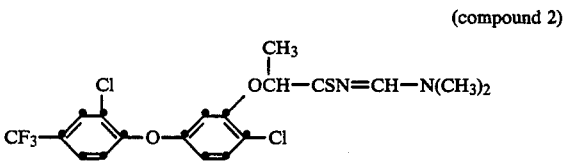

(compound 2)

20.5 g of α-[3-(2'-chloro-4'-trifluoromethylphenoxy)-6-chlorophenoxy]thiopropionylamide obtained in Example 1 are stirred for 3 hours at 40° C. with 25 ml of N,N-dimethylformamide dimethyl acetal $[(CH_3)_2-N-CH(OCH_3)_2]$. After cooling, excess acetal is removed by distillation, affording 20.6 g of the title compound in the form of a viscous oil.

The following compounds are obtained in corresponding manner:

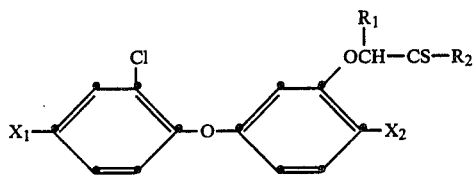

| Compound | $X_1$ | $X_2$ | $R_1$ | $R_2$ | Physical data (°C.) |
|---|---|---|---|---|---|
| 1 | $CF_3$ | Cl | $CH_2$ | $NH_2$ | m.p. 83–89° |
| 2 | $CF_3$ | Cl | $CH_3$ | $N=CH-N(CH_3)_2$ | viscous oil |
| 3 | Cl | Cl | $CH_3$ | $NH_2$ | m.p. 93–95° |
| 4 | Cl | Cl | $CH_3$ | $N=CH-N(CH_3)_2$ | viscous oil |
| 5 | Cl | Cl | $C_2H_5$ | $NH_2$ | $n_D^{26}$ 1.6660 |
| 6 | Cl | Cl | $C_2H_5$ | $N=CH-N(CH_3)_2$ | viscous oil |
| 7 | Cl | $NO_2$ | $CH_3$ | $NH_2$ | viscous oil |
| 8 | Cl | $NO_2$ | $CH_3$ | $N=CH-N(CH_3)_2$ | viscous oil |
| 9 | $CF_3$ | $NO_2$ | $CH_3$ | $NH_2$ | viscous oil |
| 10 | $CF_3$ | $NO_2$ | $CH_3$ | $N=CH-N(CH_3)_2$ | viscous oil |

FORMULATION EXAMPLES

EXAMPLE 3

Formulation examples for compounds of formula I (throughout, percentages are by weight)

| (a) Wettable powders | (a) | (b) | (c) |
|---|---|---|---|
| α-[3-(2',4'-dichlorophenoxy)-6-chlorophenoxy]thiopropionylamide | 20% | 60% | 0.5% |
| sodium lignosulfonate | 5% | 5% | 5% |
| sodium laurylsulfate | 3% | — | — |
| sodium diisobutylnaphthalene-sulfonate | — | 6% | 6% |
| octylphenol polyethylene glycol ether (7–8 moles of ethylene oxide) | — | 2% | 2% |
| highly dispersed silicic acid | 5% | 27% | 27% |
| kaolin | 67% | — | — |
| sodium chloride | — | — | 59.9% |

The active ingredient is thoroughly mixed with the adjuvants and the mixture is thoroughly ground in a suitable mill, affording wettable powders which can be diluted with water to give suspensions of the desired concentration.

| (b) Emulsifiable concentrate | (a) | (b) |
|---|---|---|
| α-[3-(2',4'-dichlorophenoxy)-6-chlorophenoxy]thiobutyrylamide | 10% | 1% |
| octylphenol polyethylene glycol ether (4–5 moles of ethylene oxide) | 3% | 3% |
| calcium dodecylbenzenesulfonate | 3% | 3% |
| castor oil polyglycol ether (36 moles of ethylene oxide) | 4% | 4% |
| cyclohexanone | 30% | 10% |
| xylene mixture | 50% | 79% |

Emulsions of any required concentration can be obtained from this concentrate by dilution with water.

| (c) Dusts | (a) | (b) |
|---|---|---|
| α-[3-(2'-chloro-4'-trifluoromethylphenoxy)-6-chlorophenoxy]-thiopropionylamide | 0.1% | 1% |
| talcum | 99.9% | — |
| kaolin | — | 99% |

Dusts which are ready for use are obtained by mixing the active ingredient with the carriers, and grinding the mixture in a suitable mill.

| (d) Extruder granulate | (a) | (b) |
|---|---|---|
| α-[3-(2',4'-dichlorophenoxy)-6-nitrophenoxy]-thiopropionylamide | 10% | 1% |
| sodium lignosulfate | 2% | 2% |
| carboxymethylcellulose | 1% | 1% |
| kaolin | 87% | 96% |

The active ingredient is mixed and ground with the adjuvants, and the mixture is subsequently moistened with water. The mixture is extruded and then dried in a stream of air.

| (e) Coated granulate | |
|---|---|
| α-[3-2',4'-dichlorophenoxy)-6-chlorophenoxy]thiopropionyl-dimethylamidine | 3% |
| polyethylene glycol 200 | 3% |
| kaolin | 94% |

The finely ground active ingredient is uniformly applied, in a mixer, to the kaolin moistened with polyethylene glycol. Non-dusty coated granulates are obtained in this manner.

| (f) Suspension concentrate | (a) | (b) |
|---|---|---|
| α-[3-(2',4'-dichlorophenoxy)-6-chlorophenoxy)-thiobutyryl-dimethylamidine | 40% | 5% |
| ethylene glycol | 10% | 10% |
| nonylphenol polyethylene glycol ether (15 moles of ethylene oxide) | 6% | 1% |
| sodium lignosulfonate | 10% | 5% |
| carboxymethylcellulose | 1% | 1% |
| 37% aqueous formaldehyde solution | 0.2% | 0.2% |
| silicone oil in the form of a 75% aqueous emulsion | 0.8% | 0.8% |
| water | 32% | 77% |

The finely ground active ingredient is intimately mixed with the adjuvants, giving a suspension concentrate from which suspensions of any desired concentration can be obtained by dilution with water.

| (g) Salt solution | |
|---|---|
| α-[3-(2'-chloro-4'-trifluoromethylphenoxy)-6-chlorophenoxy]-thiopropionyl-dimethylamidine | 5% |
| isopropylamine | 1% |
| octylphenol polyethylene glycol ether (78 moles of ethylene oxide) | 3% |
| water | 91% |

BIOLOGICAL EXAMPLES
EXAMPLE 4
Test of herbicidal activity on post-emergence application Different cultivated plants and weeds are reared from seeds in pots in a greenhouse until they have reached the 4–6 leaf stage. The plants are then sprayed with aqueous emulsions of test compound at different concentrations. The treated plants are then kept under optimum conditions of light, watering, temperature (22°–25° C.) and humidity (50–70%). The test is evaluated after 2 weeks and the state of the plants is assessed in accordance with the following rating:

9 = plants as untreated controls, no phytotoxic symptoms
7–8 = slight reversible damage
6 = reversible damage
5 = 50% damage
4 = irreversible damage
2–3 = severe damage, stunted growth
1 = plant withered The results are reported in the table below.

|  | Compound | | | | | | | | | | | | | |
|---|---|---|---|---|---|---|---|---|---|---|---|---|---|---|
|  | 1 | | | 2 | | | 4 | | | 5 | | | 6 | |
|  | Rate of application in kg/ha | | | | | | | | | | | | | |
|  | ½ | ¼ | ⅛ | 1 | ½ | ¼ | 2 | 1 | ½ | 2 | 1 | ½ | 2 | 1 | ½ |
| wheat | 4 | 6 | 7 | 6 | 7 | 7 | 7 | 9 | 9 | 6 | 8 | 9 | 6 | 7 | 9 |
| maize | 3 | 3 | 5 | 5 | 5 | 6 | 6 | 7 | 8 | 8 | 8 | 9 | 6 | 7 | 8 |
| rice | 5 | 7 | 9 | 4 | 5 | 7 | 9 | 9 | 9 | 7 | 7 | 9 | 7 | 7 | 9 |
| Abutilon sp. | 1 | 1 | 1 | 1 | 2 | 2 | 2 | 4 | 6 | 2 | 2 | 3 | 2 | 3 | 5 |
| Xanthium sp. | 1 | 1 | 2 | 1 | 1 | 3 | 3 | 4 | 5 | 2 | 2 | 3 | 2 | 3 | 5 |
| Chenopodium album | 1 | 1 | 1 | 1 | 1 | 2 | 2 | 2 | 2 | 2 | 2 | 2 | 2 | 2 | 3 |
| Ipomoea purpurea | 1 | 1 | 1 | 1 | 2 | 4 | 2 | 2 | 3 | 2 | 2 | 3 | 1 | 1 | 3 |
| Sinapis alba | 1 | 1 | 1 | 1 | 1 | 1 | 2 | 2 | 2 | 2 | 2 | 3 | 3 | 4 | 4 |
| Galium aparine | 1 | 1 | 1 | 2 | 2 | 2 | 2 | 3 | 4 | 1 | 1 | 3 | 3 | 4 | 5 |
| Viola tricolor | 1 | 1 | 1 | 1 | 1 | 1 | 2 | 3 | 4 | 1 | 1 | 1 | 1 | 2 | 2 |

The suitability of compound 1 for controlling weeds selectively in rice is investigated in another test. The following known herbicides are used as comparison compounds:
(A) 4-nitro-2',4',6'-trichlorodiphenyl ether, known from U.S. Pat. No. 3,080,225,
(B) 2',4'-dichloro-4-nitrodiphenyl ether ("nitrofen"), known from U.S. Pat. No. 3,080,225,
(C) 2-chloro-2',6'-diethyl-N-(butoxymethyl)acetanilide ("butachlor"), known from U.S. Pat. No. 3,442,945,
(D) O-[β-naphthyl]lactoanilide, known from U.S. Pat. No. 3,489,671,
(E) 1,3-dimethyl-4-(3',4'-dichlorobenzoyl)-5-para-tolyl-sulfonylimidazole, known from German Offenlegungsschrift No. 2 513 750.

The test is carried out as follows:
Rice plants which are 25 days old are transplanted into large rectangular asbestos cement containers in a greenhouse. Seeds of the weeds occurring in rice crops, namely Echinochloa crus galli, Cyperus difformis, Ammania and Rotala, are then sown between the rows of rice plants. The containers are well watered and kept at a temperature of about 25° C. and at high humidity. Twelve days later, when the weeds have emerged and reached the 2–3 leaf stage, the soil in each of the containers is covered with a layer of water to a height of 2.5 cm. Compound 2 is then applied in the form of an emulsifiable concentrate with a pipette between the rows of plants. The emulsifiable concentrate is diluted and applied such that it corresponds to a field application rate of 2 and 1 kg/ha respectively. The test is evaluated 4 weeks later in accordance with the above rating. The results of the test are reported in the following table:

| plant | Compound | | | | | |
|---|---|---|---|---|---|---|
|  | No. 1 | A | B | C | D | E |
| rice | 7 | 9 | 2 | 3 | 9 | 8 |
| echinochloa crus galli | 1 | 9 | 1 | 1 | 9 | 7 |
| cyperus rotundus | 1 | 5 | 1 | 8 | 9 | 5 |
| ammania indica | 1 | 9 | — | 8 | 1 | 6 |
| rotala indica | 2 | 9 | 2 | 8 | 9 | 9 |

Compound 1 destroys the weeds or damages them very severely, whereas damage to the rice plants is only quite insignificant.

What is claimed is:
1. A phenoxyphenoxyalkanoylthioamide of the formula I

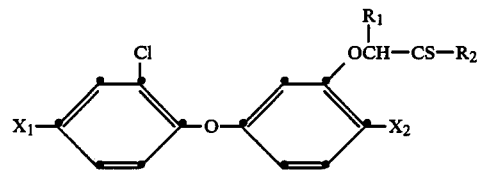

(I)

wherein $X_1$ is chlorine or trifluoromethyl, $X_2$ is chlorine, $R_1$ is $C_1$–$C_4$alkyl, and $R_2$ is the amino group or the dimethylamidino group.

2. An amide according to claim 1 of the formula Ia

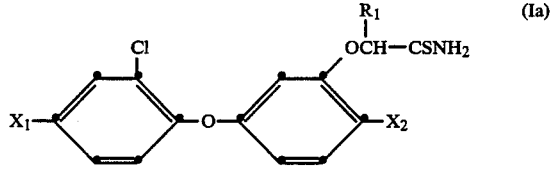

(Ia)

3. An amidine according to claim 1 of the formula Ib

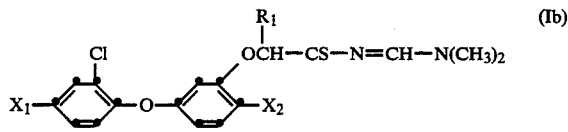

(Ib)

4. α-[3-(2'-Chloro-4'-trifluoromethylphenoxy)-6-chlorophenoxy]thiopropionylamide according to claim 2.

5. α-[3-(2',4'-Dichlorophenoxy)-6-chlorophenoxy]-thiopropionylamide according to claim 2.

6. α-[3-(2',4'-Dichlorophenoxy)-6-chlorophenoxy]-thiobutyrylamide according to claim 2.

7. α-[3-(2'-Chloro-4'-trifluoromethylphenoxy)-6-chlorophenoxy]thiopropionyl-dimethylamidine according to claim 3.

8. α-[3-(2',4'-Dichlorophenoxy)-6-chlorophenoxy]-thiopropionyl-dimethylamidine according to claim 3.

9. α-[3-(2',4'-Dichlorophenoxy)-6-chlorophenoxy]-thiobutyryl-dimethylamidine according to claim 3.

10. A herbicidal composition which contains a herbicidally effective amount of a phenoxyphenoxyalkanoylthioamide of formula I

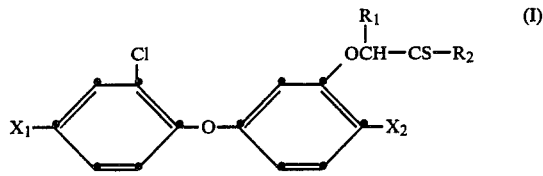

wherein $X_1$ is chlorine or trifluoromethyl, $X_2$ is chlorine, $R_1$ is $C_1$-$C_4$alkyl, and $R_2$ is the amino group or the dimethyl amidino group as active ingredient, together with inert carriers and adjuvants.

11. A method of selectively controlling weeds in crops of useful plants, which comprises treating said crops or the locus thereof with a herbicidally effective amount of a phenoxyphenoxyalkanoylthioamide of formula I

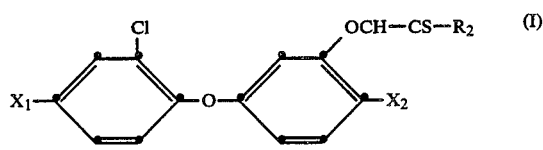

wherein $X_1$ is chlorine or trifluoromethyl, $X_2$ is chlorine, $R_1$ is $C_1$-$C_4$alkyl, and $R_2$ is the amino group or the dimethyl amidino group.

12. A method of selectively controlling weeds in cereals and rice, which comprises treating the crops or the locus thereof with a herbicidally effective amount of a phenoxyphenoxyalkanoylthioamide according to claim 11.

* * * * *